United States Patent
Razavi et al.

(10) Patent No.: US 9,078,627 B2
(45) Date of Patent: *Jul. 14, 2015

(54) INTRODUCER SHEATH WITH ELECTRODES

(75) Inventors: Mehdi Razavi, Austin, TX (US); Christopher Alexander Arevalos, Houston, TX (US); Maurice Alan Brewer, Houston, TX (US)

(73) Assignee: TEXAS HEART INSTITUTE, Houston, TX (US)

(*) Notice: Subject to any disclaimer, the term of this patent is extended or adjusted under 35 U.S.C. 154(b) by 510 days.

This patent is subject to a terminal disclaimer.

(21) Appl. No.: 13/468,774

(22) Filed: May 10, 2012

(65) Prior Publication Data

US 2012/0220848 A1    Aug. 30, 2012

Related U.S. Application Data

(63) Continuation-in-part of application No. 12/581,101, filed on Oct. 16, 2009, now Pat. No. 8,366,615, which is a continuation-in-part of application No. 12/348,658, filed on Jan. 5, 2009, now Pat. No. 8,273,023, and a continuation-in-part of application No. 12/348,695, filed on Jan. 5, 2009, now Pat. No. 8,961,417, application No. 13/468,774, which is a continuation-in-part of application No. 12/348,658, filed on Jan. 5, 2009, now Pat. No. 8,273,023, and a continuation-in-part of application No. 12/348,695, filed on Jan. 5, 2009, now Pat. No. 8,961,417.

(60) Provisional application No. 61/019,131, filed on Jan. 4, 2008.

(51) Int. Cl.
A61B 5/00 (2006.01)
A61B 5/04 (2006.01)
A61B 5/02 (2006.01)
A61B 5/053 (2006.01)
A61M 25/06 (2006.01)

(52) U.S. Cl.
CPC .............. *A61B 5/6885* (2013.01); *A61B 5/053* (2013.01); *A61B 5/6852* (2013.01); *A61M 25/0662* (2013.01)

(58) Field of Classification Search
CPC .... A61B 5/6885; A61B 5/053; A61B 5/6852; A61M 25/0662
See application file for complete search history.

(56) References Cited

U.S. PATENT DOCUMENTS

| | | | |
|---|---|---|---|
| 4,686,987 A * | 8/1987 | Salo et al. | 607/24 |
| 5,397,340 A | 3/1995 | Nyman | |
| 5,429,130 A | 7/1995 | Goldman | |

(Continued)

OTHER PUBLICATIONS

Geddes et al., Continuous measurement of ventricular stroke volume by electrical impedance, Cardiovascular Research Center Bulletin vol. 4. No. 4, Apr.-Jun. 1966, pp. 118-131.*

(Continued)

*Primary Examiner* — Reza Ghafoorian
(74) *Attorney, Agent, or Firm* — Conley Rose, P.C.

(57) ABSTRACT

An introducer comprise a sheath for introducing a catheter into a blood vessel, a plurality of electrodes on the sheath, and an impedance assessment unit provided on the sheath and connected to the electrodes. The impedance assessment unit fixes one of a current or voltage across a first pair of the electrodes and measures the other of the current or voltage across a second pair of electrodes.

20 Claims, 8 Drawing Sheets

(56) References Cited

U.S. PATENT DOCUMENTS

| | | | |
|---|---|---|---|
| 5,733,323 | A | 3/1998 | Buck et al. |
| 5,876,353 | A | 3/1999 | Riff |
| 6,076,015 | A * | 6/2000 | Hartley et al. .................. 607/20 |
| 6,351,667 | B1 | 2/2002 | Godie |
| 6,512,949 | B1 | 1/2003 | Combs et al. |
| 6,709,390 | B1 * | 3/2004 | Marie Pop .................... 600/368 |
| 6,714,814 | B2 | 3/2004 | Yamada et al. |
| 7,226,422 | B2 | 6/2007 | Hatlestsad et al. |
| 7,340,296 | B2 | 3/2008 | Stahmann et al. |
| 7,387,610 | B2 * | 6/2008 | Stahmann et al. ............ 600/538 |
| 8,366,615 | B2 * | 2/2013 | Razavi ........................... 600/371 |
| 8,483,821 | B2 * | 7/2013 | Averina et al. .................... 607/2 |
| 2003/0055461 | A1 | 3/2003 | Girouard et al. |
| 2003/0109871 | A1 * | 6/2003 | Johnson et al. ................. 606/42 |
| 2003/0212373 | A1 * | 11/2003 | Hall et al. ...................... 604/263 |
| 2005/0277912 | A1 * | 12/2005 | John ........................... 604/890.1 |
| 2005/0288726 | A1 | 12/2005 | Gollasch et al. |
| 2006/0041280 | A1 | 2/2006 | Stahmann et al. |
| 2008/0255470 | A1 | 10/2008 | Hauck et al. |
| 2008/0300504 | A1 | 12/2008 | Lefkov et al. |
| 2008/0312645 | A1 | 12/2008 | Drasler et al. |
| 2009/0171235 | A1 | 7/2009 | Schneider et al. |
| 2009/0177069 | A1 | 7/2009 | Razavi |
| 2010/0174169 | A1 | 7/2010 | Razavi |
| 2010/0174170 | A1 | 7/2010 | Razavi |
| 2011/0190756 | A1 * | 8/2011 | Venkatachalam et al. ...... 606/33 |

OTHER PUBLICATIONS

Wikipedia reference for Electrical Impedance Tomography (EIT), Found at: http://en.wikipedia.org/wiki/Electrical_impedance_tomography, 4 pages.

Office Action Dated Aug. 26, 2011 for U.S. Appl. No. 12/348,658.

Amendment and Response to Office Action Dated Aug. 26, 2011 for U.S. Appl. No. 12/348,658.

Office Action Dated Feb. 3, 2012 for U.S. Appl. No. 12/348,658.

Office Action Dated Aug. 26, 2011 for U.S. Appl. No. 12/348,695.

Amendment and Response to Office Action Dated Aug. 26, 2011 for U.S. Appl. No. 12/348,695.

Office Action Dated Feb. 2, 2012 for U.S. Appl. No. 12/348,695.

Office Action Dated Feb. 21, 2012 for U.S. Appl. No. 12/581,101.

Amendment and Response to Office Action Dated Feb. 21, 2012 for U.S. Appl. No. 12/581,101.

You, Fusheng et al., Abstract of "Monitoring Retroperitoneal Bleeding Model of Piglets by Elect Impedance Tomography," Engineering in Medicine and Biology Society, 2008, EMBS 2008, 30th Annual International Conference of the IEEE, Found at: http://ieeexplore.ieee.org/xpl/freeabs_all.jsp?arnumber=4649374, 1 page.

Wikipedia reference for Electrical Impedance Tomography (EIT), Found at: http://en.wikipedia.org/wiki/Electrical_impedance_tomography, 4 pages, Dec. 30, 2008.

* cited by examiner

| VECTOR | THRESHOLD | |
|---|---|---|
| | AMPLITUDE | PHASE |
| A | 166 | 168 |
| B | 166 | 168 |
| C | 166 | 168 |
| ⋮ | ⋮ | ⋮ |

INTRODUCER SHEATH WITH ELECTRODES

CROSS-REFERENCE TO RELATED APPLICATIONS

This application is a continuation-in-part application claiming priority to U.S. patent application Ser. No. 12/581,101 filed Oct. 16, 2009 entitled "Introducer Sheath with Electrodes", Ser. No. 12/348,658 filed Jan. 5, 2009 entitled "Introducer Sheath With Electrodes", and Ser. No. 12/348,695 filed Jan. 5, 2009 entitled "Catheter with Electrodes for Impedance and/or Conduction Velocity Measurement." Through application Ser. No. 12/348,695, the present application also claims priority to Prov. App. No. 61/019,131 filed Jan. 4, 2008 and entitled "Method, System, and Device for Detection of Pericardial Blood or Fluid." All cases listed above are incorporated herein by reference.

BACKGROUND

1. Field of the Disclosure

This invention relates generally to the field of medical devices. More specifically, the invention relates to a method and device using impedance for the detection of fluid (e.g., blood) bleeding such as pericardial effusion, retroperitoneal effusion, etc.

2. Background Information

Radiofrequency ablation (RF ablation) or other invasive cardiac procedures which involve operation within the cardiac chambers, coronary arteries or the heart's venous anatomy have saved many lives. These procedures often involve percutaneous access into the cardiac chambers or epicardial arterial or venous vessels. Catheter, pacing lead, sheath, or other types of device manipulations frequently are performed as key parts of these procedures. Example of this include balloon angioplasty or stent placement. Often, catheter access to the femoral artery is needed to enable access to the heart of elsewhere in the body.

A rare but potentially dangerous complication of these and similar procedures is inadvertent perforation of a cardiac chamber or an epicardial vessel. Retroperitoneal bleeding, arteriovenous fistula, pseudoaneurysms, and hematoma formation is also possible at the site of the insertion of the catheter into the femoral or other artery or vein. Perforations of a cardiac chamber or an epicardial vessel may lead to accumulation of blood (or other fluids) in the pericardial space or sac. This condition is referred to pericardial effusion. Cardiac tamponade is the pathophysiologic state wherein accumulation of blood or other fluid in the pericardial space or sac leads to impaired filling of the heart and a secondary decrease in cardiac output and consequential hemodynamic derangement. It is not unusual in clinical procedures for the onset of perforation to be heralded by the onset of hemodynamic derangements such as drop in blood pressure. In such cases it is frequently only at that time that the presence of a perforation is recognized. Much time may have elapsed between the creation of a perforation and the subsequent accumulation of enough blood or fluid to create a hemodynamically-significant pericardial effusion or tamponade. Of critical clinical significance is that early detection of such perforation may allow the operator to implement interventions (for example discontinuation of peri-operative anticoagulation) that would mitigate the untoward consequences of pericardial effusion.

Retroperitoneal bleeding, arteriovenous fistulae, or hematomas may lead to hematoma formation, pain, blood loss, shock, or death. Its detection is frequently only noted after hypotension or other symptoms are noted. There may be no other signs associated with bleeding. As in the case of a pericardial effusion prompt recognition offers the opportunity for potentially lifesaving intervention. Another frequent complication of such procedures involves development of blood clots ("thrombosis") within the body of the sheath. These clots may travel ("embolize") via the circulation and lead to necrosis or ischemia of tissue subserved by these blood vessels.

It follows that a method and device which could more rapidly detect the presence of pericardial or retroperitoneal bleeding, aretriovenous fistula, or hematoma, prior to the onset of symptoms, is highly desirable. Rapid detection of such bleeding or fluid accumulation can lead to more timely management—such as aborting the procedure or reversal of the patient's anticoagulation response during such cardiac procedures.

BRIEF SUMMARY

In accordance with at least one embodiment, an apparatus comprises a sheath for introducing a catheter into a blood vessel. The electrodes are provided on the sheath and many be one in number or multiple. This apparatus is usable to measure impedance for the detection of bleeding (e.g., retroperitoneal bleeding) or blood clots in the sheath itself.

In accordance with another embodiment, an apparatus comprises a sheath for introducing a catheter into a blood vessel, one or more electrodes that are provided on the sheath, one or more electrodes that are for placement remote from the sheath; and a measuring device to which at least two electrodes are coupled, and a device to create and supply a signal that is to be used to measure impedance between at least two electrodes. The measuring device measures the impedance between at least two electrodes or alternately measures the conduction velocity between the first electrode on the sheath and the second electrode.

A method embodiment is also disclosed for detecting bleeding in a person. The disclosed method comprises inserting a sheath into a blood vessel. The sheath includes at least one electrode. The method further comprises injecting, by a current source, an electrical current that runs through one pair of electrodes, computing, by logic, an impedance or conduction velocity of the injected signal between two electrodes based on the injected current, and determining, by the logic, whether the impedance or conduction velocity is at a level indicative of bleeding or a clot.

NOTATION AND NOMENCLATURE

In the following discussion and in the claims, the term "fluid" is defined to include blood and other types of body fluids or gases that may bleed or leak from a vessel or organ. All references to an impedance measurement being made encompasses any of the variations described herein as performed by the combination of the impedance assessment unit and an external apparatus.

DETAILED DESCRIPTION OF THE PREFERRED EMBODIMENTS

In accordance with preferred embodiments of the invention, a system and method are disclosed herein that involves real-time assessment of resistance or impedance to an electrical signal (current or voltage). Accumulation of sufficient fluid or blood in such areas as the pericardial space leads to changes in both the direct current (DC) resistance and/or the complex impedance to alternating current (AC) current flow. A change in either the resistance or the complex impedance signals fluid accumulation in the space through which the electrical current travels. Embodiments of the invention also use conduction time between two vectors as another variable which may be analyzed. Various embodiments are described herein for measuring impedance to detect fluid bleeding. Impedance may be computed by injecting a known current (DC or AC) and measuring the resulting voltage, or imposing a known voltage across the electrodes and measuring the resulting current. The ratio of voltage to current determines impedance.

Figure 1:
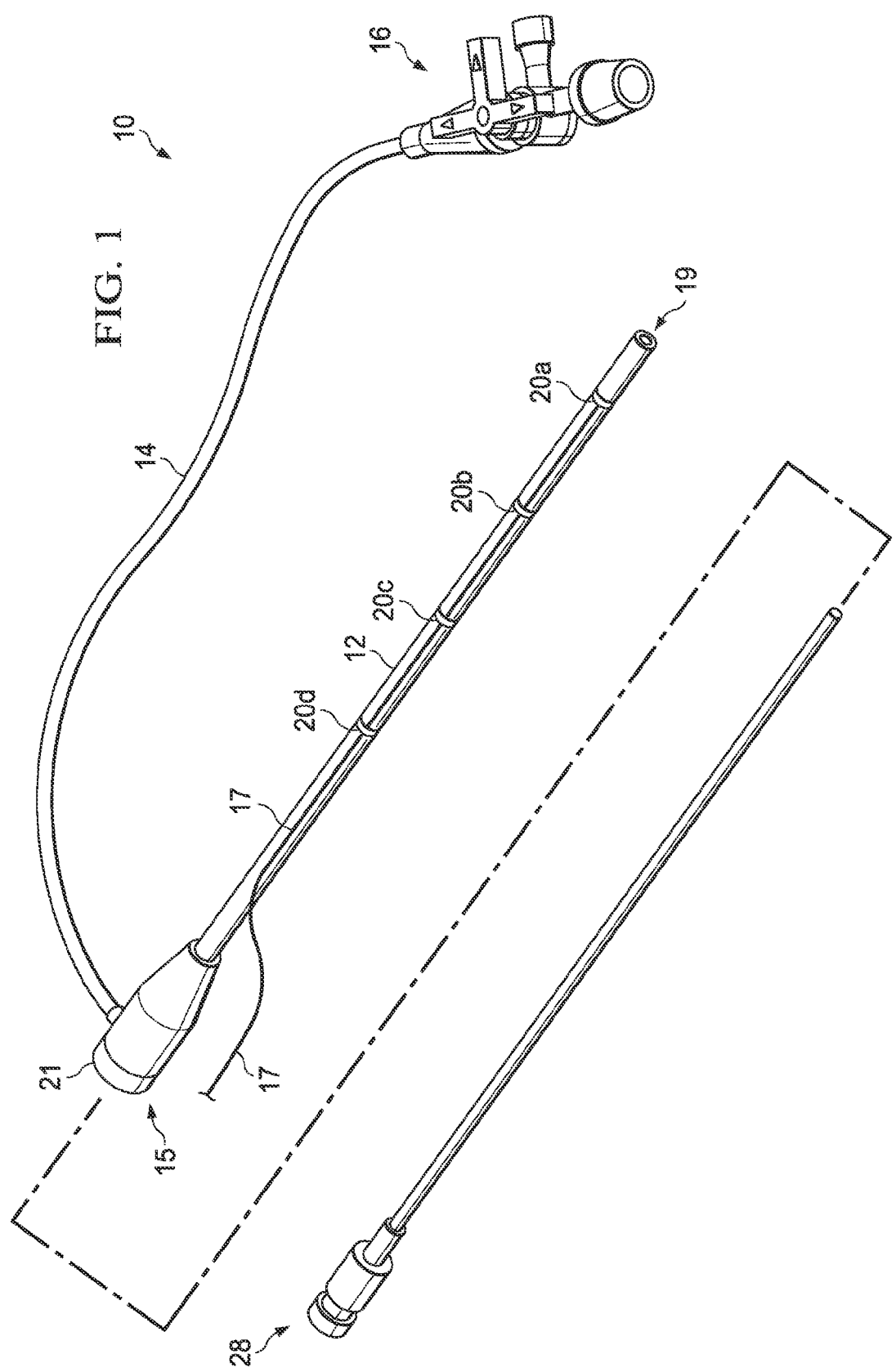
FIG. 1 shows an introducer sheath with an electrode usable to determine impedance for the detection of bleeding in accordance with various embodiments.

In accordance with one such embodiment, FIG. 1 illustrates an introducer 10 usable to insert a catheter into a blood vessel (vein or artery). The introducer comprises a hollow sheath 12 having a distal end 19 that is insertable into a blood vessel of a person. The blood vessel may be an artery or a vein. In at least one application, the blood vessel is the femoral artery, but other blood vessels may be used as well. In the illustrative embodiment of FIG. 1, multiple electrodes 20a, 20b, 20c, and 20d are provided on the sheath 12. Such electrodes can be provided at any of a variety of locations along the sheath 12. As will be explained below, the electrodes are usable to measure impedance of the person so as to detect bleeding (e.g., retroperitoneal bleeding).

Impedance between pairs of electrodes within the sheath can also be measured to assess the presence of such phenomenona as clots within the sheath. In this embodiment, the system can be based on using only one pair of electrodes such that the injected current and the detected voltage are from one pair of electrodes, or on multiple pairs of electrodes such that the injected current and the detected voltage are two separate pairs of electrodes. For example, one pair of electrodes is used to inject current and another pair of electrodes is used to measure the resulting voltage to thereby assess impedance, or vice versa (a known voltage is imposed on pair of electrodes and current is measured). Although two different pairs of electrodes are used, an electrode may be common to both pairs. Other configurations utilizing multiple electrodes are also feasible embodiments.

The sheath 12 may be coupled to a hub 15 which may incorporate a hemostasis valve 21 from which a side arm 14 may extend that allows the sheath to be used to administer fluids and or drugs. A valve 16 is provided on the opposing end of the side arm 14. The introducer 10 also includes a dilator 28 that is insertable into the hollow sheath 12. The dilator and sheath function to permit a catheter to be inserted into the blood vessel. Independently from the preceding features, the sheath 12 may also include other features to facilitate simple "peel-away" removal without disturbing a catheter having been passed the lumen of the sheath 12. Referring still to FIG. 1, electrical conductors 17 (e.g., wires) extend along at least part of the sheath 12 from the electrodes 20a-d and can be connected to an external device (i.e., a device external to the person/patient that receives the sheath 12). The conductors 17 preferably include at least one insulated conductor for each electrode 20. The conductors 17 are usable to conduct signals between at least one electrode 20 on the sheath and the external device for impedance measurements.

Figure 6:
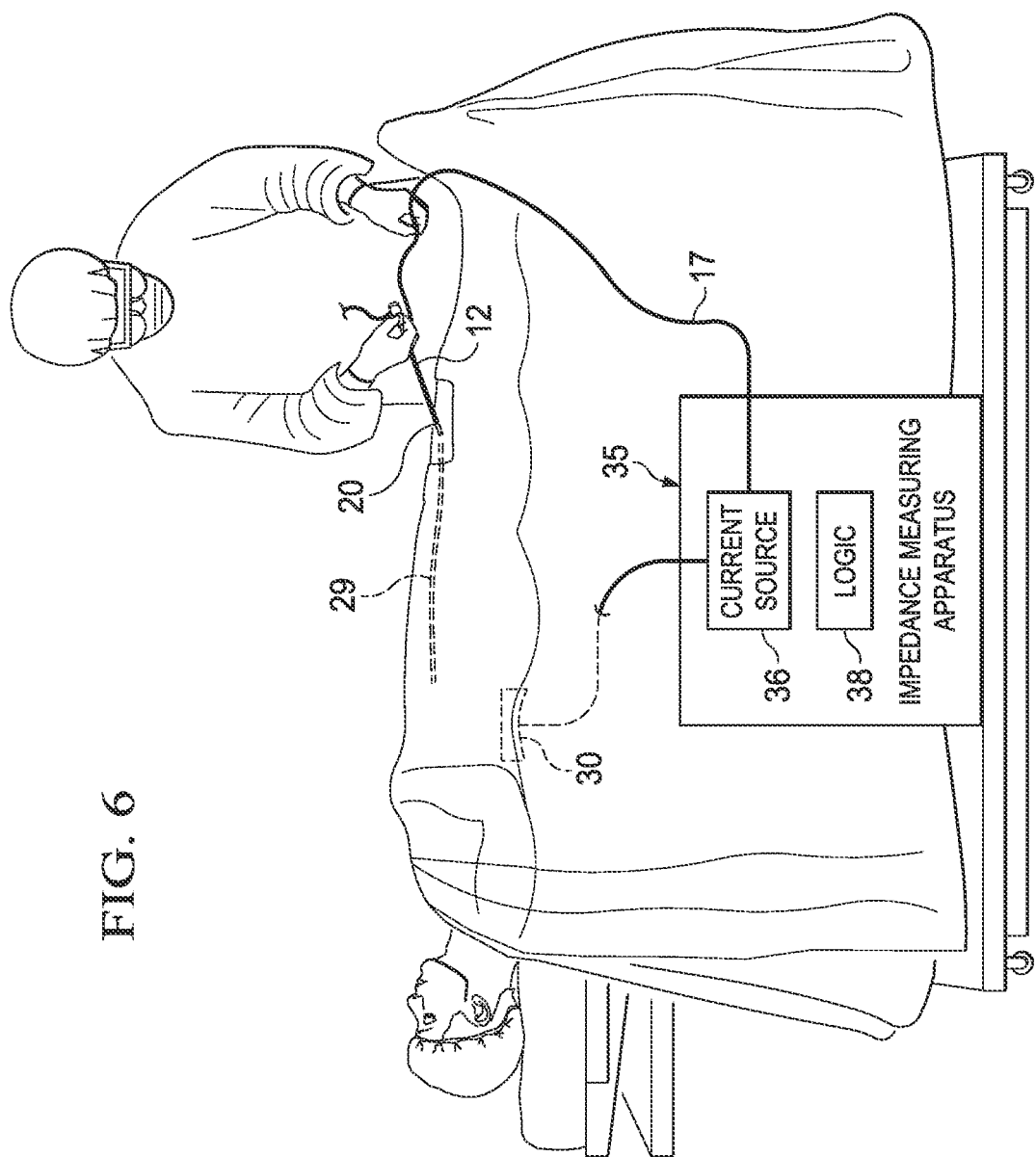
FIG. 6 depicts the sheath inserted into a blood vessel of person and connected to an impedance measuring apparatus in accordance with various embodiments.

In FIG. 1, four electrodes 20 are shown on the sheath 12, but in other embodiments, more or less than four electrodes may be provided on the sheath. Alternately only one electrode may be present on the sheath, with another electrode used in the impedance measurements being located apart from the sheath (e.g., an external electrode as illustrated in FIG. 6). Impedances between any individual pair electrodes may be measured.

Figure 2:
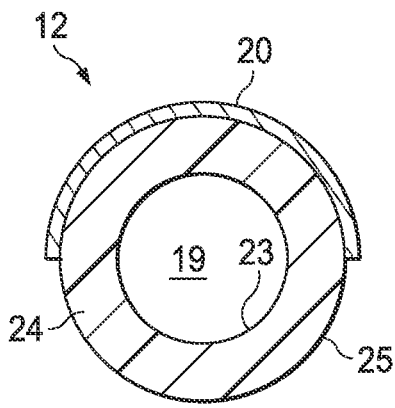
FIG. 2 shows a view of the sheath in cross-section with a partial ring electrode on an exterior surface in accordance with various embodiments.

FIGS. 2-5 illustrate various embodiments of the electrodes 20a-d. Each figure shows a view of the sheath facing distal end 19. Referring first to FIG. 2, sheath 12 comprises material 24 formed as a tubular member and comprising an inner surface 23 and an outer surface 25. In FIG. 1, the electrode 20 comprises a partial ring electrode disposed about a portion of the perimeter of the outer surface 25. In some embodiments, the electrode 20 is adhered (e.g. via glue) to the outer surface 25. In other embodiments, the electrode 20 covers more than 50% of the perimeter of the outer surface 25 and is retained (e.g., clamped) in place like a bracelet.

Figure 3:
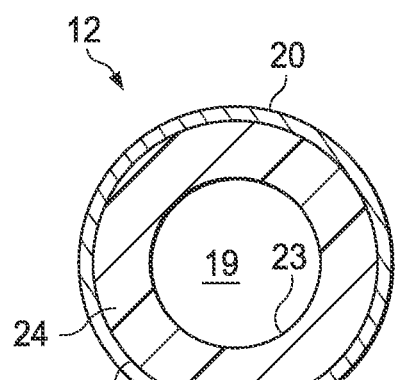
FIG. 3 shows a view of the sheath in cross-section with a complete ring electrode on the exterior surface in accordance with various embodiments.

FIG. 3 illustrates an embodiment of the electrode 20 in which the electrode is a complete ring electrode (i.e., completely surrounds the outer surface 25 of the sheath 12).

Figure 4:
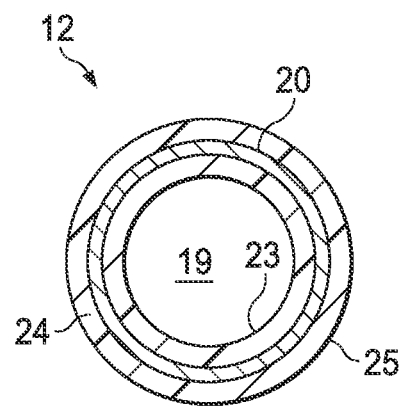
FIG. 4 shows a view of the sheath in cross-section with an electrode embedded in the material of the sheath. in accordance with various embodiments
Figure 5:
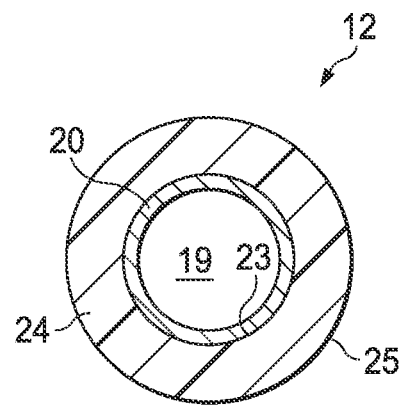
FIG. 5 shows a view of the sheath in cross-section with an electrode on an interior surface of the sheath in accordance with various embodiments.

In FIGS. 2 and 3, the electrode 20 is provided on the outer surface 25 of the sheath. In FIG. 4, the electrode 20 is embedded within the material 24 of the sheath in which case the sheath materials (or at least the segments of the sheath material between the electrodes) must be conductive of electrical signals in the range employed. Furthermore, for the purposes of detection of clot, impedance or conduction (for detecting bleeding) between these electrodes may be measured. In FIG. 5, the electrode 20 is provided on the inner surface 23 of the sheath and thus within the inner hollow portion of the sheath.

In some embodiments, the electrode 20 is located on the sheath so that the electrode will be inside the blood vessel once the sheath is inserted into the vessel. In other embodiments, the electrode may be provided on the sheath at the proximal end outside the blood vessel (and perhaps even outside the person's body). In such embodiments, the electrode 20 preferably is provided on the inner surface of the sheath (similar to that shown in FIG. 5). Normally, the sheath is filled with body fluid (e.g., blood).

FIG. 6 illustrates a person lying supine with the sheath 12 inserted into a blood vessel 29. The conductors 17 from the electrodes 20 are connected to an impedance measuring apparatus 35. The impedance measuring apparatus 35 comprises a current source 36 and logic 38. The current source 36 may be part of the logic 38 if desired. One or more additional electrodes 30 is also connected to the impedance measuring apparatus 35. Such an additional electrode is also herein referred to as the non-sheath electrode or the non-sheath electrodes. The current source 36 injects an electrical current through one of the electrodes 20 or 30. The current then passes through the person's tissues, into the other electrode and back to the current source. The injected current may comprise a series of pulses or a sustained current. The amplitude of the current may be in the sub-physiological range such as 1 milliamp. If a pulse train is used, the pulse width may be 0.2 milliseconds or less and have a frequency of between 5,000 and 500,000 Hz or higher.

The current source 36 or logic 38 measures the voltage across the electrodes 20, 30 resulting from the current, and computes the ratio of the voltage to current to compute impedance. The impedance is altered in the presence of bleeding and thus can be correlated to bleeding such as retroperitoneal bleeding. The device may also calculate the conduction time between the electrodes. Bleeding will also alter the conduction time between tissues. Alternatively, rather than a current source, a voltage source can be used to impose a specified voltage on the electrodes 20, 30 and the resulting current level is measured to compute impedance.

The non-sheath electrodes 30 may be located at any of a variety of locations. The illustrative embodiment of FIG. 6 shows the non-sheath electrode 30 attached to the skin on the person's back as a patch electrode. In other embodiments for detecting retroperitoneal bleeding, the non-sheath electrode 30 can be attached to a urinary catheter, a rectal temperature probe, an electrosurgical grounding pad, or a patch on a lateral aspect of the back as desired, separately or in combination.

In accordance with at least some embodiments, the sheath 12 may comprise two or more electrodes 20. Another pair of electrodes may be attached to the patient's skin (e.g. back, abdomen) as noted above. One pair comprising one of the sheath electrodes and one of the skin electrodes is used to inject current and the other pair of electrodes (i.e., the other sheath electrode and skin electrode) is used to measure the resulting voltage for the impedance computation.

In another embodiment, the sheath 12 may include four electrodes as shown in FIG. 1. Two electrodes are placed distally near the distal tip 19 and two are placed proximally of the shaft of the sheath. A current is sent through one distal electrode, through the patient's body to one of the proximal electrodes (the direction of current flow can be in the opposite direction as well). The remaining pair of electrodes measures the voltage for the impedance computation.

In some embodiments, each possible pair of electrodes is used to send/receive current with the remaining electrodes used to measure voltage for an impedance computation.

In some embodiments, each possible pair of electrodes is used to send/receive current with the remaining electrodes used to measure voltage for an impedance calculation. The system may cycle through each such electrode pair combination.

In yet other embodiments, the sheath may not have any electrodes. Instead, multiple electrodes (e.g., 5 or more) are placed on the patient's abdomen near the tip of electrode-less sheath. As before, each possible electrode combination is cycled through the process of sending the current, conducting the current, measuring the voltage, and computing the impedance.

Figure 7:
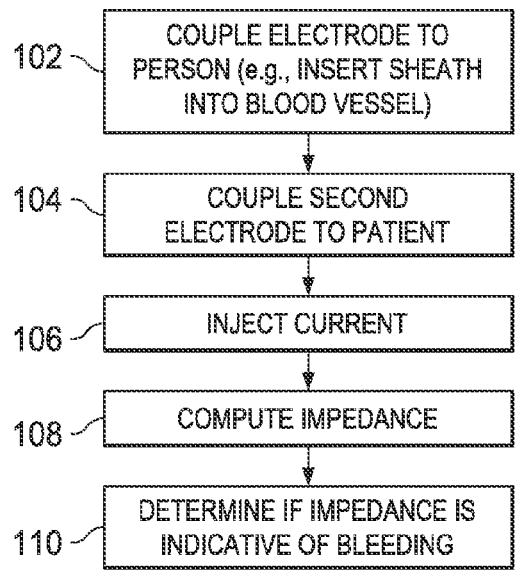
FIG. 7 shows a method in accordance with various embodiments.

FIG. 7 shows an illustrative method. At 102, an electrode is coupled to the person. In the embodiments of FIGS. 1-6, one or more electrodes are located on an introducer sheath 12 and coupled to a person as the sheath is inserted into a blood vessel. At 104, one or more non-sheath electrodes are also coupled to the person (e.g., back electrode 30 as shown in FIG. 6). At 106, upon a user activating a control on the impedance measuring device to begin the impedance measuring activity, the impedance measuring apparatus 35 injects current and, at 108, computes the impedance (e.g., measures the voltage and computes the ratio of voltage to current).

At 110, the impedance measuring apparatus 35 determines if the impedance is indicative of bleeding. In some embodiments, the logic 38 of the impedance (or conduction time) measuring apparatus 35 compares the computed impedance to a predetermined threshold, derived threshold based on baseline measurements at the onset of the procedure, otherwise defined acceptable range. The logic 38 determines that bleeding has occurred if the computed impedance or conduction time is outside of the acceptable range for the threshold as previously defined. If bleeding has been detected, the logic 38 may alert a user via an audible and/or visual indicator.

In some embodiments, the impedance measuring apparatus 35 injects a known current and measures the resulting voltage to determine impedance. In other embodiments, the impedance measuring apparatus 35 applies a known voltage to the electrodes and measures the resulting current to determine impedance.

It may be desirable to leave the sheath 12 in place in the person's blood vessel following the completion of the medical procedure (e.g., RF ablation) for which the sheath was used in the first place. It is possible that bleeding (e.g., retroperitoneal bleeding) will begin after the completion of the medical procedure. With the sheath 12 still in place, impedance measurements can be made via the impedance measuring apparatus 35 to detect post-medical procedure completion onset of bleeding. A user of the impedance measuring apparatus can activate a control (e.g., press a button) on the impedance measuring apparatus to activate an impedance/bleed monitoring.

Besides retroperitoneal bleeding, arteriovenous fistulae, or hematomas, other types of internal bleeding may occur as well. For example, during a catheterization procedure of a patient's heart or surrounding blood vessel(s), bleeding can occur into the pericardial space. In accordance with various embodiments, a catheter includes one or more electrodes, at least one of which is used to make impedance measurements as described above to detect bleeding such as pericardial effusion. In another embodiment of this invention the tip of the catheter or electrode may be located on any guide wire used during coronary intervention (a wire over which a coronary stent or angioplasty apparatus may be advanced is always utilized during such procedures). In this embodiment, the guide wire is or contains an electrode. In such a situation the impedance between the tip of the wire and any second electrode as described elsewhere (such as a skin patch electrode) can be utilized. In another embodiment a distal and proximal electrode (relative to the location of coronary blockage which is to be angioplastied or stented) within the same wire may be used to assess progression of clot formation or perforation and effusion.

Figure 8:
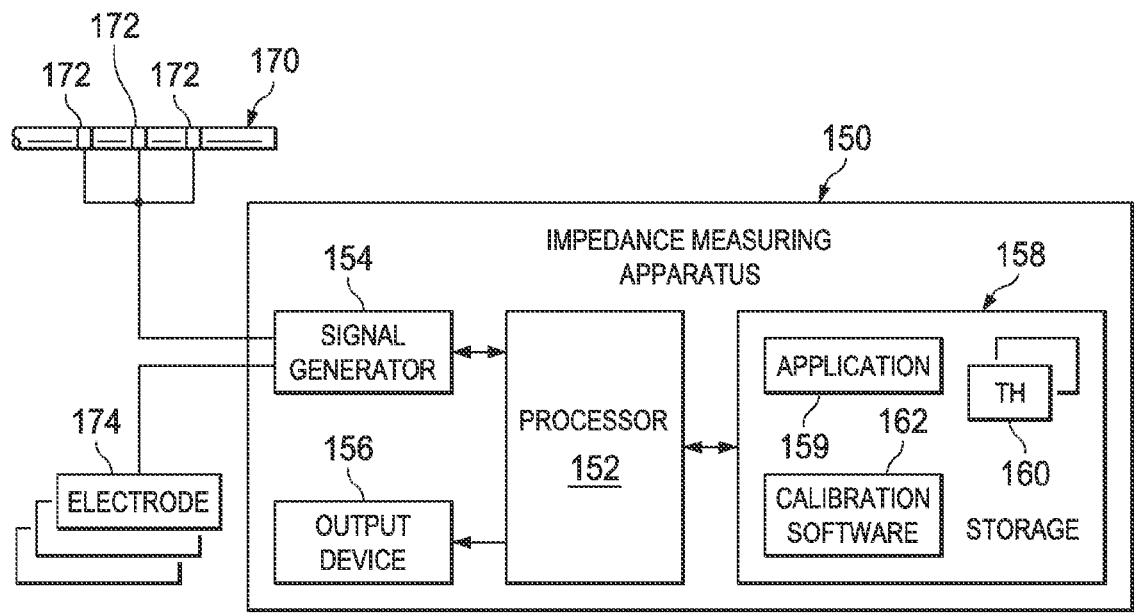
FIG. 8 shows an impedance measuring apparatus in accordance with various embodiments.

FIG. 8 illustrates an embodiment of an impedance measuring apparatus 150 usable to measure impedance and detect bleeding. Any of the attributes described below for impedance measuring apparatus 150 can apply to impedance measuring apparatus 35 of FIG. 6 as well. The impedance measuring apparatus 150 comprises a processor 152, a detector 153, a signal generator 154, an output device 156 and storage 158. The storage 158 comprises volatile memory (e.g., random access memory), non-volatile storage (e.g., read only memory, hard disk drive, Flash storage, etc.), or combinations thereof. The storage 158 comprises an application 159 usable to perform impedance measurements and detect bleeding as described herein and calibration software 162. Both applications 159 and 162 are executed by processor 152. Storage 158 is also used to store one or more impedance thresholds 160. The impedance measuring apparatus 150 comprises logic which includes any combination or all of the processor 152, signal generator 154, and storage 158 (and associated applications and thresholds stored thereon).

Electrodes 172 are provided on a catheter 170 and electrically coupled to the signal generator 154. One or more additional electrodes 174 may also be provided and coupled to signal generator 154. Under control of the processor 152 (via execution of application 159), the signal generator 154 selects one pair of electrodes 172, 174, applies a known current to one of the electrodes in the selected pair and receives the current via the electrode. The detector 153 determines the resulting voltage across a selected pair of electrodes, which may be the same pair or a different pair of electrodes from that pair used to apply the voltage, and provides the voltage measurement to the processor 152. The detector 153 may comprise an analog-to-digital converter to convert the voltage measurement to digital form for the processor. Both the current and voltage values are provided to the processor which then computes the impedance (ratio of voltage to current), or conduction time and compares the computed impedance or conduction time to a corresponding threshold to determine if bleeding has occurred. A pair of electrodes can be selected coupling two of the electrodes 172, 174 to the signal generator (via a switching device). The signal generator can select two electrodes from among electrodes 172 on the catheter, two electrodes from among electrodes 174, or one electrode each from electrode sets 172 and 174.

If two electrodes 172 are selected on the catheter 170, the impedance measuring apparatus 150 can detect a blood clot within the catheter by measuring the impedance between the two catheter electrodes. The same is true with respect to the embodiment of FIG. 1. The sheath 12, in some embodiments, comprises more than one electrode 20. The impedance measuring apparatus 35 measures the impedance between the electrodes on the sheath to detect blood clots that may form within the sheath.

The catheter 170 can be inserted into any of a variety of veins or arteries. In one embodiment, the catheter 170 is inserted into the femoral artery (for detection, for example, of retroperitoneal effusion), the heart or coronary vasculature such as the coronary sinus (for detection of pericardial effusion), or other blood vessels or anatomic structures. The coronary sinus is an epicardial vein through which venous drainage of coronary circulation occurs. It is on the inferior surface of the left atrium. More distally this structure turns into the great cardiac vein or any of its other tributaries.

The electrodes 174 may be located at any of variety of sites. An electrode 174, for example, may be located on the person's esophagus, on the person's skin, or on the person's heart. Moreover, impedance can be measured for detecting bleeding between, for example, the coronary sinus and skin, coronary sinus and esophagus, skin and skin (e.g., patient's front and back), heart and coronary sinus, heart and esophagus, two sites on the same catheter, two sites on the same sheath, two sites on the same vein and femoral artery to skin.

As explained herein, more than two electrodes can be used for measuring impedance. Impedance can be measured between any pair of electrodes and such an impedance measurement represents a vector. For example, in a three-electrode system (first, second, and third electrodes), there are three possible impedance vectors including the impedance between the first and second electrodes, the impedance between the first and third electrodes, and the impedance between the second and third electrodes. The number of vectors increases disproportionately with increasing numbers of electrodes. The physical location of the various electrodes may be useful to detect bleeding in different locations. For example, bleeding may occur between the first and second electrodes, but the fluid (e.g., blood) may not be present between the second and third electrodes. Thus, in this example, the impedance vector associated with the first and second electrodes may be indicative of the bleed, but not so the impedance vector associated with the second and third electrodes or possibly the first and third electrodes. Moreover, more than two electrodes provides an enhanced ability to detect bleeding in different locations than might be possible in a two-electrode only system.

In some embodiments, the computed impedance may be resistance while in other embodiments, the computed impedance is complex having both amplitude and phase components. In other embodiments the computed variable is conduction velocity. Further, the impedance measuring apparatus 150 (or impedance measuring apparatus 35 in FIG. 6) determines and stores an impedance threshold for each impedance vector. Two or more of the various impedance thresholds may be the same or the impedance thresholds may all be different. Each impedance threshold may be an amplitude only value (resistance) or, in the case of complex impedance, comprise an amplitude value and a phase value.

Figures 9, 10:
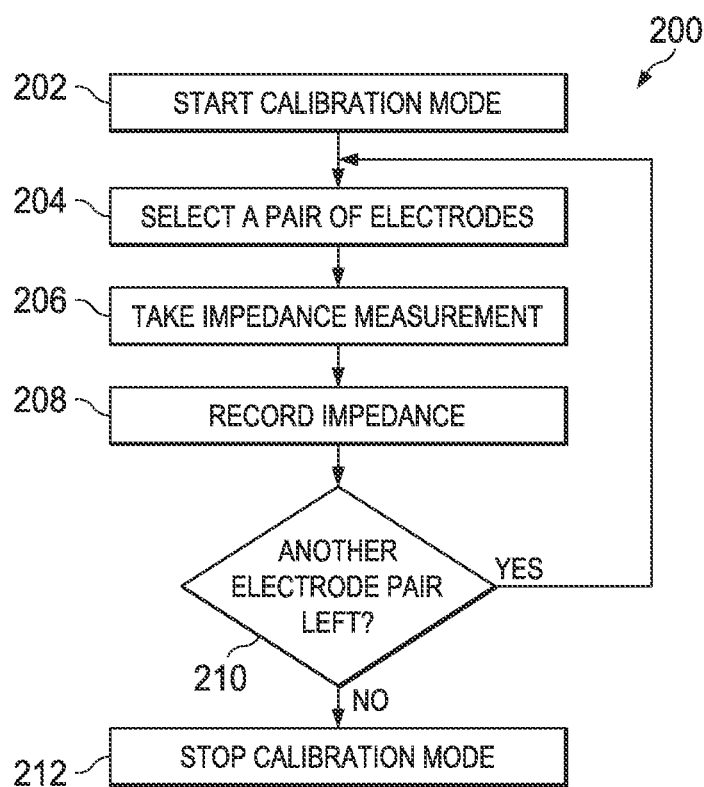
FIG. 9 illustrates various impedance thresholds stored in the impedance measuring apparatus.
FIG. 10 depicts an illustrative method of calibrating the impedance measuring apparatus.

FIG. 9 illustrates the thresholds 160 as a table comprising one or more vectors A, B, C, etc. Each vector represents a pair of electrodes. For each vector, there is an amplitude threshold value 166 and/or a phase threshold value 168. In some embodiments, the impedance measuring apparatus detects the presence of bleeding if either of the amplitude or phase of the computed impedance for a given vector exceeds its corresponding amplitude or phase value. In other embodiments, the impedance measuring apparatus detects a bleed only if both the computed amplitude and phase exceed their corresponding threshold counterparts. The threshold counterparts may have been derived in a variety of ways one of which may be baseline measurements at the beginning of the procedure for each individual patient as explained below.

FIG. 10 illustrates a method 200 for calibrating the impedance measuring apparatus (35 or 150) for the various thresholds. In some embodiments, the impedance measuring apparatus comprises a calibration mode that can be initiated by a user of the impedance measuring apparatus (e.g., by pressing a button). The processor of the impedance measuring apparatus executes the calibration software 162 (impedance measuring apparatus 35 may also have similar software to be executed by a processor). FIG. 10 is a method performed by the processor upon executing the calibration software 162. The calibration mode is performed preferably before the medical procedure [e.g., coronary angiography (after the wire has been placed through the blockage but before angioplasty)

or electrophysiology study (after catheters have been placed in the coronary sinus but before delivery of radiofrequency ablation)] begins.

The calibration mode begins at 202. A pair of electrodes is selected at 204 and at 206 and 208, an impedance measurement is taken and the computed impedance is recorded (e.g., stored in storage 158) (as amplitude and/or phase values). Preferably, the impedance measurement for a selected pair of electrodes is taken over the course of several breaths by the patient. The impedance computed for the selected impedance vector will vary during a respiratory cycle. By taking the impedance measurement over the course of several breaths (e.g., 10 seconds), the impedance measuring apparatus can account for the normal variations in impedance. The threshold (amplitude or phase) may be computed as an average during the recording period or may be set as the peak value detected (or a value slightly higher (e.g., 5% higher) than the peak). At 210, the impedance measuring apparatus determines whether there is an additional impedance vector for which a threshold is to be determined. If there is, control loops back to step 204 at which such an electrode pair is selected. If not more electrode pairs are to be selected, than the calibration mode stops at 212. This calibration process may take several minutes. The same calibration variables may be measured for conduction velocities.

Once the calibration process is completed, the medical procedure (which might result in bleeding or clot formation) can begin. Any bleeding will be detected a change in impedance above deviating from an impedance threshold (e.g., an increase above the threshold or decrease below the threshold).

The impedance measuring techniques described herein to detect bleeding are also usable to detect a hemothorax. In this application, electrode locations would include the anterior chest and posterior chest walls, the esophagus at the level near the heart, the trachea, as well as numerous intravascular and intra-cardiac and intra-coronary locations. The electrodes may be on catheters or wires.

With regards to conduction velocity, the logic (e.g., that contained in the measuring devices described herein) assesses the conduction time between the onset of the electrical impulse in the first (transmitting) electrode and second (receiving) electrode. These electrodes are identical to the electrodes described in embodiments of this invention. The electrical output is in the same range with regards to frequency and amplitude. The measured variable, however, is the difference (delta) in time (usually milliseconds) between onset of stimulus (electrical output) in the transmitting electrode and sensing of that impulse (electrical sensing) in the receiving electrode. Conduction velocity is heterogeneous with variations in tissue characteristic. As fluid develops, the conduction velocity between the transmitting and receiving electrode will also change. This will be noted as a deviation from a baseline values (similar to the impedance values/thresholds described herein). An alert will then be issued. The various embodiments of apparatus and methods described above can also be used to measure conduction velocity and use conduction velocity to determine thickening of the heart and the presence of fluid bleeding.

Figure 11:
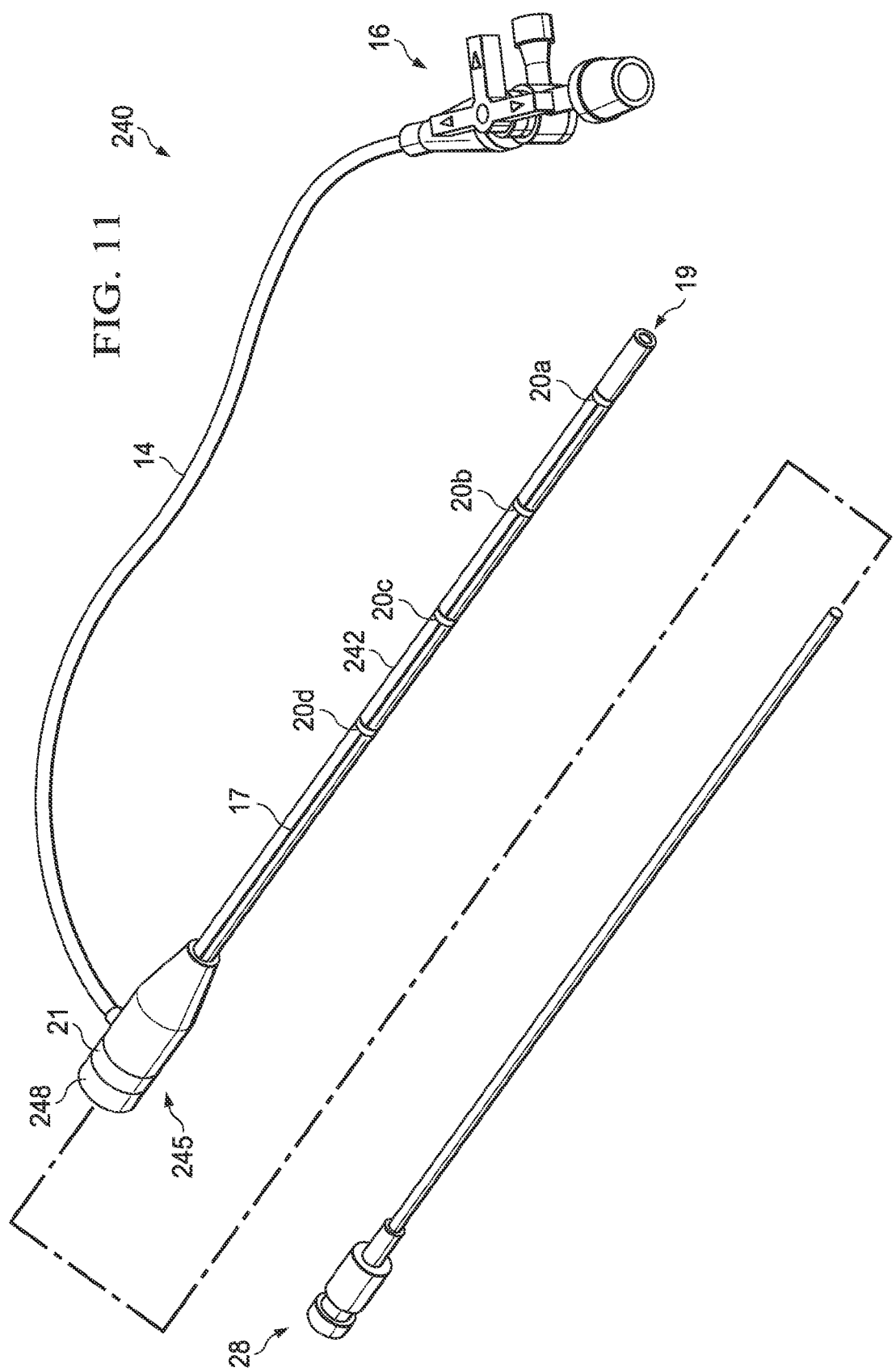
FIG. 11 shows an introducer containing an impedance assessment unit in accordance with various embodiments.

In accordance with some embodiments, the sheath 12 includes a wireless transceiver that is able to wireless transmit impedance values or impedance-related values to an external apparatus rather than via a wired connection as shown in FIG. 6. The embodiment of introducer 240 in FIG. 11 is similar in some ways to introducer 10 of Figure. Introducer 240 includes sheath 242 which includes multiple electrodes 20a-20d as well a hub 245. Hub 245 includes an impedance assessment unit 248.

As will be explained below, the impedance assessment unit 248 connects to the electrodes via conductors 17 and is used during an impedance measurement. The impedance assessment unit may include a power source. In one embodiment, the impedance assessment unit sets a predetermined current or voltage for one pair of electrodes and measures the resulting voltage or current from another electrode pair. The impedance assessment unit may also include a wireless transmitter to transmit the measured voltage/current to the external apparatus which in turn computes impedance based on the received, measured voltage/current and aprior knowledge of the predetermined current/voltage set by the impedance assessment unit 248. Alternatively, the impedance assessment unit 248 may also wirelessly transmit the current/voltage it set to the external apparatus. Further still, the impedance assessment unit 248 may itself compute the impedance value and wirelessly transmit the computed impedance value to the external apparatus. These and other embodiments are discussed below.

Figure 12:
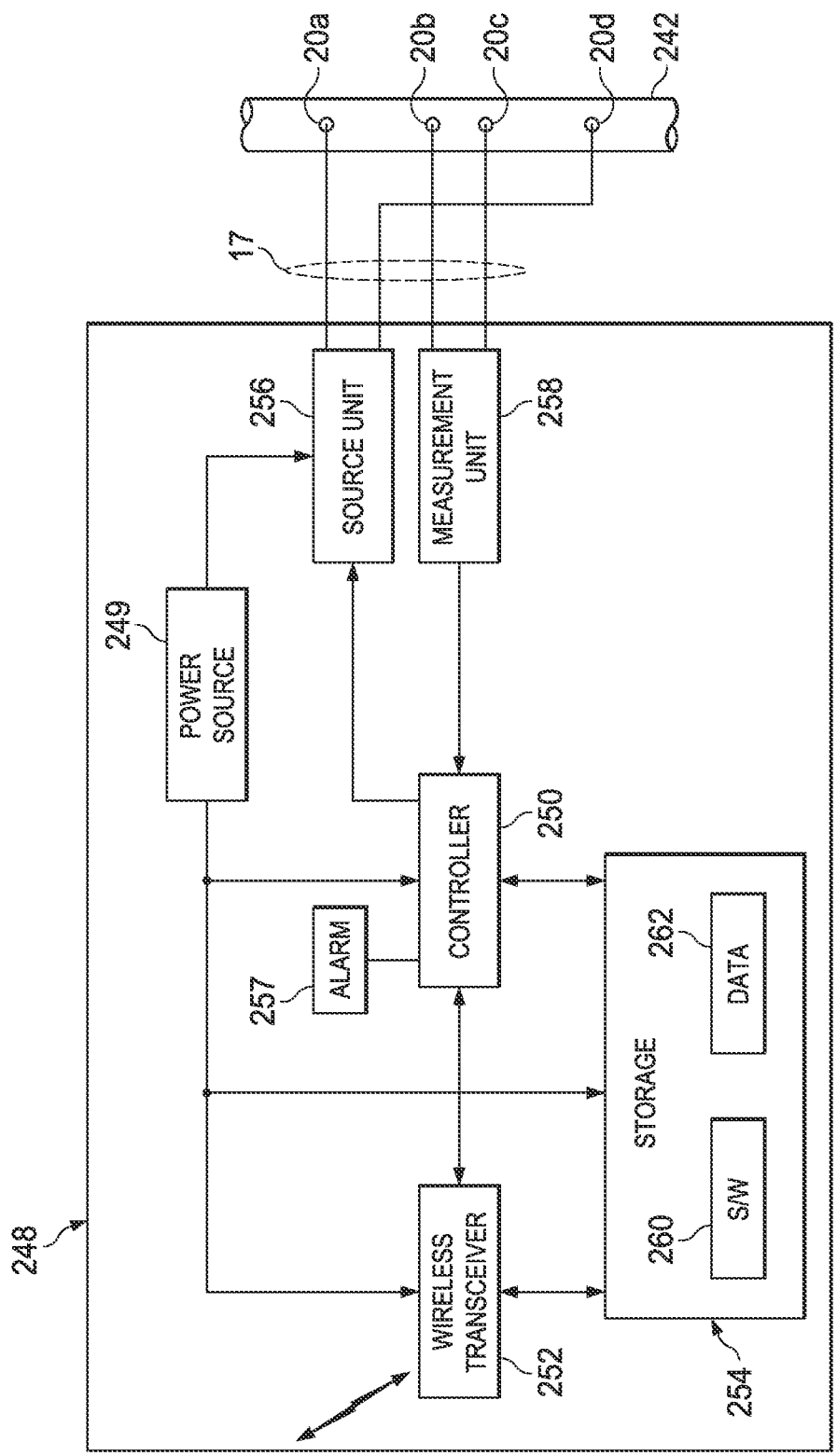
FIG. 12 shows a block diagram of the introducer of FIG. 11 in accordance with various embodiments.

FIG. 12 shows a block diagram of the impedance assessment unit 248. As shown in the example of FIG. 12, the impedance assessment unit 248 includes a power source 259, a controller 250, a wireless transceiver 252, storage 254, a source unit 256, an alarm 257, and a measurement unit 258.

The power source 249 may comprise a battery (disposable or rechargeable), a charged capacitor, a wireless power receiver, or other sources of electrical power. The power source 249 provides electrical power to the controller 250, wireless transceiver 252, storage 254 and source unit 256.

The controller 250 executes software 260 provided on storage 254. The controller 250, upon executing software 260, provides the impedance assessment unit 248 with some or all of the functionality described herein. The storage 254 may comprise volatile storage (e.g., random access memory), non-volatile storage (e.g., flash storage, read only memory, etc.), or combinations of both volatile and non-volatile storage. Data 262 consumed or produced by the software can also be stored on storage 254. For example, measured current or voltage values, computed impedance values, etc. can be stored on storage 254 pending wireless transmission through the wireless transceiver 252 to an external apparatus.

The wireless transceiver may be implemented in accordance with any suitable wireless protocol such as BLUETOOTH, WiFi, etc. The transceiver may be capable of transmitting only, or may be capable of transmitting and receiving. The controller 250 causes the wireless transceiver to transmit values indicative of impedance (current, voltage) or impedance values themselves. The transceiver 252 may be a bi-directional device to permit outgoing transmissions of data, as well as receive incoming commands from an external apparatus. For example, an external apparatus may send a command to the controller 250 via the wireless transceiver 252 to command the impedance assessment unit 248 to initiate a process by which impedance is determined, or to transmit previously stored data (e.g., current, voltage, and/or impedance).

The source unit 256 receives power from the power source 249 and generates a current or voltage under control by the controller 250. The source unit 256 may generate a predetermined current or voltage, and is broadly referred to as a source unit to indicate either or both possibilities. The source unit 256 is connected to a pair of electrodes (electrodes 20a and 20d in the example of FIG. 12), As a current source, the source unit 256 injects a current through one of the electrodes 20a,d and receives the return current through the other of the electrodes 20a,d.

The measurement unit 258 measures the resulting voltage or current. That is, if the source unit 256 injects a predetermined current into the patient, the measurement unit 258 measures the resulting voltage. If the source unit 256 imposes a predetermined voltage across electrodes 20a,d, the measurement unit 258 measures the resulting current. In either case, the measurement unit 258 provides the measured electrical parameter to the controller 250.

The controller 250 thus knows the magnitude of the predetermined current or voltage generated by the source unit 256 and the magnitude of the measured voltage or current from the measurement unit 258. As such, the controller 250 can compute impedance, and do so as the ratio of voltage to current and transmit the computed impedance to the external apparatus. However, as noted above, the controller 250 may not compute impedance and instead transmit the measured electrical parameter (voltage or current) to the external apparatus for the external apparatus to compute impedance. The external apparatus may or may not know what predetermined current or voltage was set by the source unit 256. If the external apparatus does know the magnitude of the source unit's current/voltage, that value need not be (but of course can be) transmitted to the external apparatus. If the external apparatus is not aware of the source unit's current/voltage magnitude, the controller 250 preferably transmits both the measured voltage/current from the measurement unit 258 and the source unit's predetermined current/voltage.

Figure 13:
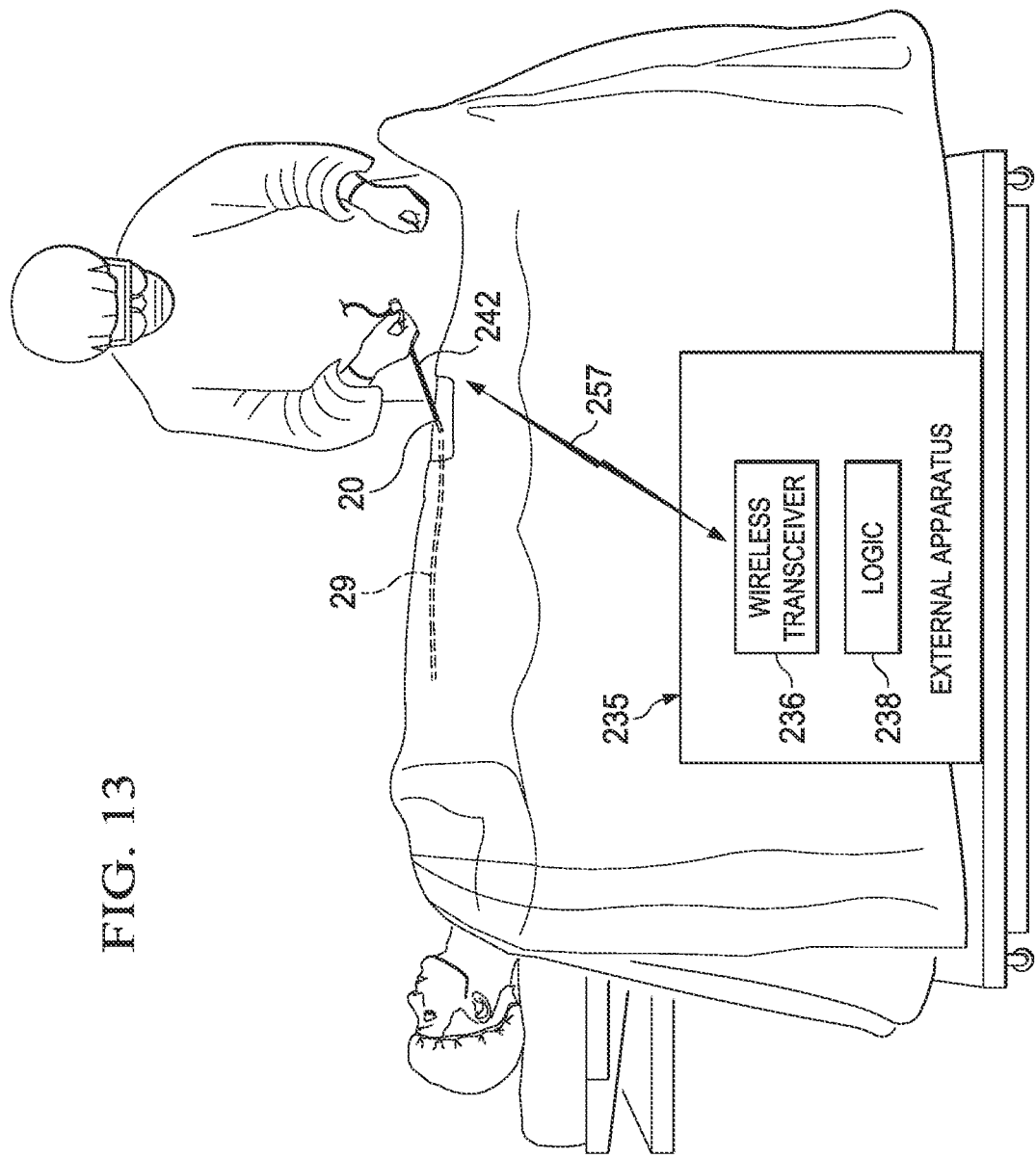
FIG. 13 illustrates use of the introducer of FIG. 11 in accordance with various embodiments.

FIG. 13 illustrates an application of the use of the impedance assessment unit 248. Sheath 242 containing impedance assessment unit 248 is inserted into a patient's blood vessel as shown and a wireless communication link 257 is established to an external apparatus 235. The external apparatus 235 may contain a corresponding wireless transceiver 236 as well as logic 238. The external apparatus may be computer (desktop, laptop, notebook, etc.), a smart phone, or any other type of device capable wirelessly interacting with the impedance assessment unit 248 of sheath 242. In some embodiments, the external apparatus is, or is built into, a bedside monitor.

Regardless of whether the impedance assessment unit 248 computes impedance or transmits the necessary data for the external apparatus to compute the impedance, the computed impedance may be resistance based on DC current/voltage. In other embodiments, AC current/voltage is used and complex impedance is computed as a magnitude and a phase. AC currents/voltages have an associated frequency and impedance measurements can be made at any one or more of multiple different frequencies. All references to an impedance measurement being made encompass any of the variations described herein as performed by the combination of the impedance assessment unit and an external apparatus.

Impedance measurements made at certain frequencies may provide more useful information than at other frequencies. At certain frequencies, it may be difficult to detect a bleed, where as other frequencies, bleed detection is easier. Further, the particular frequenc(ies) useful to detect a bleed may vary from patient to patient. Accordingly, a calibration is performed at the beginning of a procedure using a sheath as described above. The calibration may entail performing multiple impedance measurements at various frequencies. In some implementations, the range of acceptable frequencies is from 1000 Hz to 200 KHz, although a different frequency range may be acceptable as well. Within the frequency range multiple discrete frequencies are chosen to make the impedance measurement. For example, 10 KHz may be chosen as well as 1000 Hz, and 100 KHz.

The source unit 256 may be capable of injecting an AC current (or generating an AC voltage) at various frequencies as commanded by the controller 250. The controller 250 preferably is configured (e.g., by way of software 260) to initiate multiple impedance measurements at various frequencies during the calibration process. Each measured electrical parameter (e.g., voltage) may be stored in data 262 in storage 254 and mapped to the frequency of the source signal (e.g., current) that caused the measured voltage to occur. Thus, multiple AC voltages (or current) may be stored in storage 254, one voltage (or current) corresponding to each AC current (or voltage) frequency. The measured parameters may be kept in storage 254 and/or wirelessly transmitted to the external apparatus 235.

The calibration process may be initiated in any suitable manner. For example, a wireless command to initiate the calibration process may be transmitted from the external apparatus 235 to the impedance assessment unit 248. Alternatively, impedance assessment unit 248 may have a user input control (e.g., a button, switch, etc.) that a user can activate to initiate the calibration process. Further still and in the case in which the power source is a battery, an electrically insulative strip may prevent at least one of the battery's contacts from connecting the to the rest of the impedance assessment unit 248 circuitry. Removal of the strip may cause the controller 250 to initialize and start the calibration process.

Then, at predetermined time periods (e.g., once per minute) after calibration, the controller 250 initiates additional impedance measurements to be made. At the expiration of each such time period, the controller 250 may also causes multiple impedance measurements to be initiated at the same frequencies used during the calibration process. After computing the impedance values at the various frequencies (whether the impedance assessment unit or the external apparatus makes the computation as explained above), a comparison is made between each such impedance value and a previously computed impedance value. The previously computed impedance value may be the impedance value computed during calibration or any other previously computed impedance values. A determination is made as to whether the difference, as an absolute value, between the impedance value and the previously computed impedance value (e.g., calibration impedance value) is greater than a predetermined threshold. An impedance difference greater than the threshold is an indicator of a bleed. Another way to make the comparison is compute a ratio of the current impedance value to the previously computed impedance value and then compare the ratio to a predetermined range. A ratio being outside the range is an indicator of a bleed. Bleeds may be easier to detect at certain frequencies rather than others for certain patients and thus the probability is higher that an actual bleed will be detected if multiple frequencies are used.

The process of taking impedance measurements and comparing to a previous impedance value (e.g., calibration impedance values) is repeated at the expiration of each subsequent time period. Additionally or alternatively, the impedance assessment unit 248 may be triggered manually to initiate an impedance measurement. The user can activate the user control noted above, if such a user control is provided, or the external apparatus 235 may wirelessly transmit a command to cause the controller 250 to initiate a new impedance measurement.

Referring again to FIG. 12, in embodiments in which the impedance assessment unit 248 computes impedance, the controller 250 may activate he alarm 257 if a potential bleed is detected. The alarm may be a visual indicator such as a light emitting diode (LED), an audible indicator such as a piezoelectric device, or both. While the embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. Accordingly, the scope of protection is not limited by the description set out above, but is only limited by the claims which follow, that scope including all equivalents of the subject matter of the claims.

The discussion of a reference in the Background Information is not an admission that it is prior art to the present invention, especially any reference that may have a publication date after the priority date of this application. The disclosures of all patents, patent applications, and publications cited herein are hereby incorporated herein by reference in their entirety, to the extent that they provide exemplary, procedural, or other details supplementary to those set forth herein.

What is claimed is:

1. An introducer, comprising:
    a sheath for introducing a catheter into a blood vessel at an insertion site;
    a plurality of electrodes on the sheath; and
    an impedance assessment unit provided on said sheath and connected to said electrodes, said impedance assessment unit includes a power source, a wireless transceiver and is configured to inject one of a known current or known voltage across a first pair of the electrodes and measures the other of the current or voltage across a second pair of electrodes;
    wherein the impedance assessment unit is configured to compute an impedance based on the current and voltage and detect a bleed at the insertion site based on the computed impedance;
    wherein the impedance assessment unit is configured to transmit a value indicative of the bleed through the wireless transceiver to an external apparatus.

2. The introducer of claim 1 wherein the impedance assessment unit comprises a controller, a source unit and a measurement unit, wherein the controller is configured to cause the source unit to provide the known current or voltage to the first pair of electrodes and receive from the measurement unit a measured value of the current or voltage.

3. The introducer of claim 2 wherein the controller is configured to initiate impedance measurements at multiple different frequencies.

4. The introducer of claim 2 wherein the controller is configured to receive a command via the wireless transceiver to initiate an impedance measurement.

5. The introducer of claim 1 wherein the known current or voltage is an alternating current (AC) current or voltage.

6. The introducer of claim 5 wherein the impedance assessment unit initiates multiple impedance measurements by serially injecting the known current or voltage at various predefined frequencies while simultaneously measuring the other of the current or voltage.

7. The introducer of claim 6 wherein the impedance measurement unit computes impedances based on multiple currents and voltages, and detects the bleeding through comparison of each computed impedance to a baseline impedance.

8. The introducer of claim 1 wherein a magnitude or frequency of the known current or voltage is variable by the impedance assessment unit.

9. The introducer of claim 1 wherein the wireless transceiver is a bi-directional wireless transceiver configured to receive a signal from an external device and transmit a value indicative of the bleeding to the external device.

10. The introducer of claim 9 wherein the received signal includes a command to take an impedance measurement.

11. The introducer of claim 9 wherein the received signal includes a command to program an amplitude or frequency of the known current or voltage.

12. The introducer of claim 9 wherein the value indicative of the bleed includes an alarm signal.

13. The introducer of claim 1 wherein the impedance assessment unit is configured to make a plurality of impedance measurements and average the measurements together.

14. The introducer of claim 1 wherein the impedance assessment unit is configured to compare the computed impedance value to a previously computed impedance value.

15. The introducer of claim 14 wherein the impedance assessment unit is configured to compute the time rate of change of the computed impedance value relative to a previously computed impedance value.

16. The introducer of claim 1 further comprising an indicator activated by the impedance assessment unit upon detection of the bleed.

17. The introducer of claim 16 wherein the indicator is at least one of a visual indicator and an audible indicator.

18. The introducer of claim 1 wherein the impedance assessment unit comprises a current source and a voltage monitor.

19. The introducer of claim 1 wherein the impedance assessment unit comprises a voltage source and a current monitor.

20. The introducer of claim 1 wherein the sheath has a hub and the impedance assessment unit is provided in the hub.

* * * * *